United States Patent
Klunder et al.

(10) Patent No.: US 9,134,244 B2
(45) Date of Patent: Sep. 15, 2015

(54) WIREGRID MONITOR DEVICE

(75) Inventors: Derk J. W. Klunder, Eindhoven (NL); Maarten M. J. W. Van Herpen, Eindhoven (NL); Hendrik R. Stapert, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 457 days.

(21) Appl. No.: 12/526,547

(22) PCT Filed: Feb. 12, 2008

(86) PCT No.: PCT/IB2008/050503
§ 371 (c)(1),
(2), (4) Date: Aug. 10, 2009

(87) PCT Pub. No.: WO2008/099339
PCT Pub. Date: Aug. 21, 2008

(65) Prior Publication Data
US 2010/0108908 A1    May 6, 2010

(30) Foreign Application Priority Data

Feb. 12, 2007 (EP) ..................................... 07102146
Oct. 26, 2007 (EP) ..................................... 07301503

(51) Int. Cl.
*G01N 21/64* (2006.01)
*B82Y 15/00* (2011.01)

(52) U.S. Cl.
CPC .............. *G01N 21/648* (2013.01); *B82Y 15/00* (2013.01); *G01N 21/6452* (2013.01)

(58) Field of Classification Search
None
See application file for complete search history.

(56) References Cited

U.S. PATENT DOCUMENTS

| | | | |
|---|---|---|---|
| 6,124,597 A * | 9/2000 | Shehada et al. | 250/461.2 |
| 6,455,861 B1 * | 9/2002 | Hoyt | 250/458.1 |
| 6,790,671 B1 | 9/2004 | Austin et al. | |
| 2003/0132392 A1* | 7/2003 | Kuroda et al. | 250/397 |
| 2003/0174992 A1 | 9/2003 | Levene et al. | |
| 2005/0046847 A1* | 3/2005 | Cromwell et al. | 356/417 |
| 2006/0209413 A1 | 9/2006 | Kim et al. | |

FOREIGN PATENT DOCUMENTS

| | | |
|---|---|---|
| WO | 2006135782 A2 | 12/2006 |
| WO | 2006136991 A1 | 12/2006 |

(Continued)

OTHER PUBLICATIONS

Wenger et al: "Single Molecule Fluorescence in Rectangular NANO-Apertures"; Optics Express, vol. 13, No. 18, August 2005, pp. 7035-7044.

(Continued)

*Primary Examiner* — Costantine Hannaher (57) ABSTRACT

A device for monitoring radiation emitted by luminophores present in an analyte fluid of a wiregrid biosensor. The monitoring device comprises a non-polarized light source (41) for illuminating the wiregrid biosensor for exciting fluorescent labels arranged in the analyte fluid of said biosensor. A detector (71) detects radiation emitted by the labels after excitation. A polarizing filter (53) is arranged in between the transparent substrate and the detector for suppression of background emission radiation from labels positioned outside apertures in the wiregrid, in the analyte fluid.

20 Claims, 6 Drawing Sheets

(56) References Cited

FOREIGN PATENT DOCUMENTS

| | | |
|---|---|---|
| WO | 2007010428 A2 | 1/2007 |
| WO | 2007072415 A2 | 6/2007 |

OTHER PUBLICATIONS

Weiss, S.: "Fluorescence Spectroscopy of Single Biomolecues"; Science, vol. 283, pp. 1676-1683.

* cited by examiner

WIREGRID MONITOR DEVICE

FIELD OF INVENTION

The present invention relates to the field of biosensors and more specifically to a sub-diffraction-limited biosensor.

BACKGROUND OF THE INVENTION

Biosensor technology is well known in the art.

US Patent Application No. 2003/0174992 discloses a method and an apparatus for providing a zero-mode waveguide including an analyte, which is subjected to activation by electromagnetic radiation for analysing the analyte.

WO 2006/136991 entitled "Luminescence sensors using sub-wavelength apertures or slits", discloses a biosensor with sub-wavelength spatial resolution.

WO 2007/072415 entitled "Luminiscence sensor operating in reflection mode", discloses a method for detection of fluorescent radiation generated by molecules in an aperture.

Such a bio sensor may comprise a non-transparent material arranged on a substrate of a transparent material and forming at least one aperture for being filled with said analyte fluid. The apertures have a first in-plane dimension below the diffraction limit of the excitation light in the medium inside the apertures and a second in-plane dimension above the diffraction limit of the excitation light in the medium inside the apertures. The aperture-plane is defined by a first vector directed along the first in-plane dimension of the aperture and a second vector directed along the second in-plane dimension of the aperture. Such a wire grid has a transmission axis where light that is polarized, such that the electric field is parallel with a transmission-plane, that is defined by the first vector and a third vector that is normal to the aperture-plane, below called T polarized light, is essentially transmitted and light that is polarized such that the electric field is orthogonal to the transmission-plane, below called R polarized light, is substantially blocked.

An analyte is applied to the biosensor and penetrates into the apertures. The analyte comprises a target molecule to be analyzed. The target molecule is labeled with a luminophore and the aggregate of luminophores/target molecule is immobilized at a substrate side of the apertures while free luminophores and luminophores attached to target molecules are present at an analyte side of the apertures in the analyte. The immobilized luminophores correspond to a qualitative or quantitative representation of the target molecule to be analysed.

Emission radiation from the immobilized luminophores is determined by a detector. In order to discriminate the desired radiation of the immobilized luminophores from background radiation of the free luminphores and the target molecules labeled with a luminophores, the background radiation has to be suppressed. The background radiation may be several orders of magnitude larger than the useful radiation from the immobilized luminophores. The substantial suppression of the luminescent background radiation enables essentially background free measurements that would otherwise require rinsing, but rinsing may not take place for example during real-time measurements. For a practical wire grid biosensor illuminated with polarized excitation light, the suppression of background radiation is limited to about three orders of magnitude. This limited background suppression, ultimately results in a reduction in the accuracy and surface-specificity of the sensor. Furthermore, there is a need in the art for a biosensor that can use a non-polarized light source, such as a light emitting diode, LED, which is cheaper and may produce a larger output power.

SUMMARY OF THE INVENTION

Accordingly, an object of the present invention is to mitigate, alleviate or eliminate one or more of the above-identified deficiencies and disadvantages singly or in any combination.

According to an aspect of the invention, there is provided a device for monitoring radiation emitted by luminophores present in an analyte fluid, comprising: a biosensor having at least one non-transparent material arranged on a substrate of a transparent material and forming at least one aperture for being filled with said analyte fluid having a first in-plane dimension, which is smaller than half an effective wavelength of radiation in the biosensor and a second in-plane dimension which is larger than half an effective wavelength of radiation of the bio sensor, and has a plane of transmission; an excitation source for exciting luminophores present in the analyte fluid of said biosensor; a detector for detecting radiation emitted by the luminophores upon excitation; and a polarizing filter arranged in between the biosensor and the detector. The detector may be arranged at a substrate side of the bio sensor. The excitation source may be a light source emitting polarized light, such as polarized light having an elliptical polarization such as circular or linear polarization, or said excitation source may be a light source emitting non-polarized light. The polarizing filter may be arranged for substantially attenuating radiation with an electric field parallel to a plane of transmission of the aperture. The polarizing filter may be rotatable.

In an embodiment the light source comprises a band pass filter for passing radiation having a wavelength pass band corresponding to an absorption wavelength band for excitation of said luminophores, and for blocking radiation having a wavelength corresponding to an emission wavelength of said luminophores. Furthermore, a wavelength pass filter may be arranged before the detector for passing radiation having a wavelength corresponding to an emission wavelength of said luminophores and blocking radiation passed by said band pass filter.

In another embodiment the polarizing filter may comprise a polarizing beam splitter passing radiation having a polarization plane parallel with the transmission plane of the aperture towards said detector, and reflecting or blocking radiation having a polarization orthogonal to the transmission plane of the aperture towards a second detector or the polarizing filter may comprise a dicroic mirror arranged to direct said excitation radiation towards the biosensor and to pass emission radiation to the detector.

In a further embodiment, the radiation from said light source may be arranged to pass said polarizing filter before illuminating the biosensor.

In a still further embodiment, the light source may be arranged on the substrate side of the biosensor, and detection is performed in a reflection mode. Alternatively, the light source may be arranged on the analyte fluid side of the biosensor, and detection is performed in a transmission mode. The light source may emit light having a low coherence length, such as having a bandwith larger than about 1 nm.

The device may comprise an analyte fluid and the analyte may comprise a target molecule and a luminophore, such as a fluorophore, in a medium, which is comprised in said aperture. A capture molecule may be arranged adjacent a substrate end portion of the aperture, said capture molecule being intended to form an aggregate with said target molecule and luminophore. The analyte fluid may be arranged on one side of the substrate comprising said apertures and the detector and the polarization filter are arranged at the other side of the substrate.

BRIEF DESCRIPTION OF THE DRAWINGS

Further objects, features and advantages of the invention will become apparent from the following detailed description of embodiments of the invention with reference to the drawings, in which.

DETAILED DESCRIPTION OF EMBODIMENTS

Below, several embodiments of the invention will be described with references to the drawings. These embodiments are described in illustrating purpose in order to enable a skilled person to carry out the invention and to disclose the best mode. However, such embodiments do not limit the invention. Moreover, other combinations of the different features are possible within the scope of the invention.

A biosensor according to the embodiments described below may comprise an analyte arranged in apertures defined in a material that is non-transparent for at least one of the exitation and the luminescence light, typical examples are Aluminum, Gold, Silver, Chromium, having a first in-plane dimension below the diffraction limit of the excitation light in the medium inside the apertures and a second in-plane dimension above the diffraction limit of the excitation light in the medium inside the apertures. By in-plane dimension is meant the dimension in a plane parallel to the substrate.

The analyte may be included in a fluid. A luminophore present in the fluid will emit electromagnetic radiation when exposed to excitation energy. The emitted radiation is collected by a detector.

The total emitted radiation energy, i.e. the sum of the radiation energy of the individual luminophores emitted by the luminophores, has a predetermined relationship to a property of the analyte such as being proportional to a concentration of a molecule of the analyte. By analysing the emitted radiation, properties of the analyte can be determined, quantitatively and/or qualitatively.

A method for immobilizing analyte molecules at the bottom of each aperture will be described herein-after. Each analyte molecule is provided with a luminophore, such as a fluorescent label. By exciting the luminophore and collecting the emitted radiation, a detection of the analyte molecule may be provided. The detection can be qualitative and/or quantitative.

Ligands or capture molecules may be arranged or immobilized at specific portions of the aperture, said ligands forming luminophores when contacted by a target molecule of the analyte. Such formation of luminophores may take place in different manners, such as described in the article: "Fluorescence spectroscopy of single biomolecules" by S. Weiss, Science, Vol. 283, pp 1676-1683, the technical contents of which are hereby incorporated by reference. The ligands may immobilize the luminophores so that they emit radiation from the immobilized positions at excitation.

The ligands may be immobilized in trenches arranged in a substrate adjacent to the bottom of the apertures.

The luminophores may be excited to emit radiation in different manners, such as by electric or chemical energy. The emitted radiation may take place by different physical processes, such as luminescence, phosphorescence, fluorescence, Raman scattered light, Hyper-Raman scattered light or Hyper-Rayleight scattered light etc. The emitted radiation may be electromagnetic radiation, such as light, including infrared light.

Luminophores which are excited with electromagnetic radiation will be considered, specifically light, including ultraviolet, visible and infrared light, with a wavelength in the relevant medium that is at least twice as large as the first in plane dimension of the aperture. The effective wavelength is the wavelength of the radiation in vacuum divided by the refractive index of the medium.

The luminescent radiation emitted by the luminophore can be detected at either side of the biosensor. If the analyte fluid is present on a front side, the radiation can be detected at a back side of the substrate. When a light source is directed towards the substrate from the back side thereof, R-polarized excitation light will establish an evanescent field inside the apertures, while T-polarized excitation light will establish a propagating wave inside the aperture. Such an evanescent field may excite the luminophores present in the aperture adjacent the substrate side. The evanescent field will have an exponential decay in the aperture from the substrate side of the aperture. Thus, luminophores present close to the substrate side of the aperture will be more efficiently excited than luminophores present at or outside the analyte side of the aperture. Excitation light which is non-polarized or with other polarization states, such as circularly, elliptically, or linearly polarized light that is a linear combination of R and T polarized light, can be decomposed into R and T polarized light and will result in a combination of evanescent and progating excitation light inside the aperture.

The generated luminescent radiation will in general have a polarization state with both R and T polarized components. The T polarized fraction of the luminescent light will be essentially transmitted by the aperture, while the R polarized component will be substantially suppressed by the aperture.

In many applications, a background attenuation of about 1000 would be sufficient, but one would rather use a non-polarized light source, such as a light emitting diode, LED, which is typically less expensive than a laser and may still provide the required excitation power.

Figure 1:
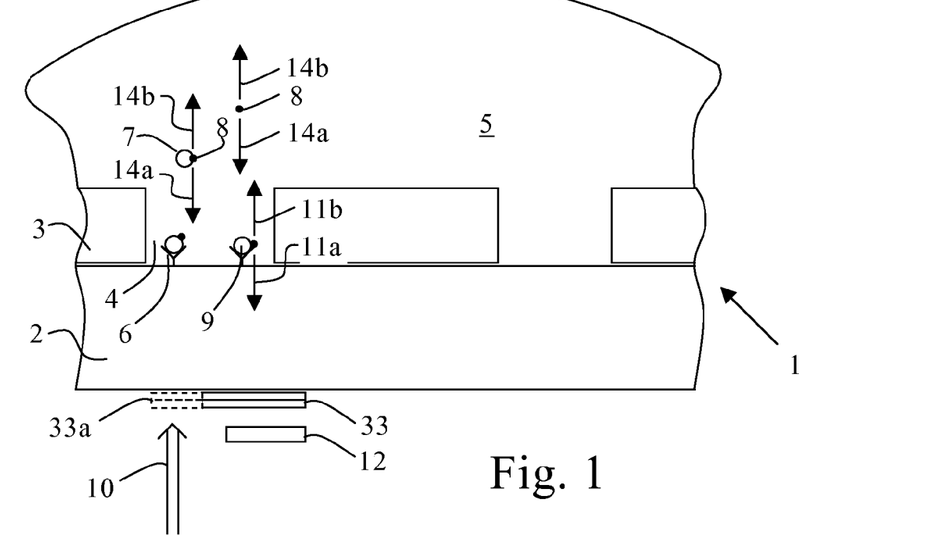
FIG. 1 is a schematic illustration for explaining the principles.

FIG. 1 discloses a system according to a first embodiment. The system comprises a wiregrid biosensor, for example of the type disclosed in WO 2007/072241.

The biosensor 1 comprises several "wires" 3 arranged on a transparent substrate 2. The substrate may be made from glass, silica or other similar material, such as acrylic glass, epoxy resin, polyvinylchloride (PVC), etc. In order to be sufficiently transparent, the material should have a refractive index with an imaginary part smaller than $10^{-4}$. The wires may be formed by a metal, such as gold, aluminium, silver, chromium, etc, which is etched or plated to obtain the desired structure, i.e. the plurality of apertures 4. Formation of such wires and a wiregrid is known in the art, see for example WO 2006/136991.

A plurality of apertures 4 are formed between the wires 3. The aperture has a sub-diffraction-limited dimension in a first in-plane direction. This first in-plane dimension is smaller than half the effective wavelength of the excitation radiation. If water (n=1.3) is present in the aperture and the excitation radiation has a wavelength in vacuum of 633 nm, the effective wavelength will be 487 nm and the first in-plane dimension of the apertures is smaller than half the effective wavelength being 243 nm. The first in-plane dimension may be smaller than 0.25 times the effective wavelength or 121 nm. The first in-plane dimension may be smaller than 0.2 times the effective wavelength or 97 nm. The first in-plane dimension may be smaller than 0.15 times the effective wavelength or 73 nm. The second in-plane dimension of the aperture is larger than half the effective wavelength, such as at least 0.5 times the effective wavelength or at least 243 nm. The second in-plane dimension may be 10 to 100 times the effective wavelength, or 4.9 to 49 μm. The second in-plane dimension may be 100 to 1000 times the effective wavelength, or 49 to 490 μm. The second in-plane dimension may be at least 1000 times the effective wavelength, or at least 490 μm.

An analyte fluid 5 may be introduced in the apertures of the biosensor. The analyte may comprise target molecules 7 provided with labels of a luminophore or fluorophore 8 that is able to emit electromagnetic radiation upon excitation.

The substrate 2 may be provided with capture molecules or ligands 6 that exhibit an affinity towards the target molecules 7 and being immobilized at the surface of said substrate 2 at the bottom or substrate side of the aperture. When a target molecule 7 comes sufficiently close to a ligand 6, the target molecule is caught by the ligand and forms an aggregate 9 comprising a ligand 6, a target molecule 7 and a fluorophore 8. The target molecule and the label or fluorophore attached thereto becomes immobilized at a position close to the substrate side of the aperture 4.

The biosensor 1 is exposed to excitation radiation 10 from an external radiation source, comprising for example light at a wavelength of about 700 nm. Other wavelength radiation may be used as well such as microwaves, infrared light, near-infrared (NIR) light, visible light, ultraviolet light, X-ray, etc.

In case of circularly polarized light, the excitation radiation can be decomposed into (about) 50% T- and (about) 50% R-polarized radiation. As a result (about) 50% of the excitation radiation is substantially transmitted and the other (about) 50% of the excitation radiation generates an evanescent field inside the aperture that decays exponentially and is essentially not transmitted. Substantial suppression of the excitation light for positions away from the sample facet of the wiregrid, therefore requires that the light is essentially R-polarized.

The biosensor may be operated in reflection mode. The biosensor is exposed to excitation radiation 10 directed towards the substrate end of the apertures.

The aggregate 9 comprising a fluorophore 8 immobilized adjacent the substrate side will absorb excitation energy and emit fluorescent radiation in all directions, depending on the direction of the transition dipole moment, the fluorescent is more or less pronounced in some directions, as indicated by arrows 11a and 11b. A portion 11a of the emitted radiation is directed towards a detector 12 arranged below the substrate 2, while another portion 11b is directed towards the analyte side of the aperture.

Even when properly polarized excitation light is used, a small fraction η of the excitation light (for a typical aperture as described above the transmitted R-polarized excitation light is a factor 1/1000 of the incident R-polarized excitation light 10) is transmitted by the aperture. This transmitted fraction η can be absorbed by fluorophores 8 present in the fluid 5 at the analyte side of the aperture and excite such fluorophores to emit radiation as indicated by arrows 14a and 14b. The emitted radiation has in general both T- and R-polarized components. The fluid may comprise free target molecules 7 provided with fluorophores 8, as well as free fluorophores 8. The portion of the radiation indicated by arrows 14a will pass through the aperture and the portion of such radiation that is T-polarized will, in contrast to R-polarized components be transmitted by the aperture and give rise to undesired background radiation.

If a large amount of external fluorophores 8 that are not bound to ligands 6 is present in the fluid 5 at the analyte side of the apertures, such background radiation will be large. Such external fluorophores may be reduced by rinsing, but rinsing may not take place for example during real-time measurements.

It is noted that, typically, the largest portion of the radiation 14a from fluorophores present in the fluid 5 at the analyte side and passing through the aperture at the substrate side, is T-polarized light. A small fraction, which is about 0.5*η, of the radiation 14a that passes the aperture is R-polarized light.

A polarization filter 33 is arranged before the detector 12. The polarizing filter has a high suppression, which is equal or better than the suppression 1/η of an aperture, such as more than 10,000 for T-polarized light. Thus, most of the radiation 14a from the fluorophores present in the fluid 6 will be blocked by the filter 33. Thus, the background radiation will be reduced by the factor between 0.5*η and η depending on the suppression of filter 33, which is a substantial reduction. The useful radiation, or the radiation to be detected 11a, will also be reduced, but only with a minor factor. Thus, an improvement of the signal-to-background ratio of between 0.5/η and 1/η has been obtained by means of the filter 33.

The filter 33 can have an attenuation factor of at least the same as said wiregrid attenuation factor η, but may have a still larger attenuation factor of more than about 10η. Such polarizing filters are commercially available, such as Glan-laser polarizers with a typical attenuation factor of 100000.

The polarization filter 33 may be a wiregrid similar to the biosensor 1, in which case the polarizing filter 33 has the same suppression η as the wiregrid. In this case, the suppression will only be 50% of the theoretically maximally obtainable improvement.

A further reduction of the background radiation may be obtained by using R-polarized excitation radiation. In this case, the excitation radiation will be attenuated when passing the aperture by said attenuation factor η, which means that the background radiation reaching the detector 12 will be reduced by a factor of $0.5*\eta^2$ to $\eta^2$ depending on the attenuation factor of filter 33, i.e. in the case indicated above by a factor of 500,000.

The same polarizing filter 33 may be used for both the excitation radiation and for blocking background radiation to the detector, as indicated by broken lines 33a in FIG. 1.

Excitation radiation reflected from the substrate 2 and the wiregrid would also reach the detector as background radiation. Such excitation background radiation can be reduced by different measures, such as filters passing only the fluorescent emitted radiation. The excitation radiation can also be directed towards the biosensor at an angle, so that the reflected radiation does not reach the detector. In this case, scattered excitation radiation directed towards the detector can be removed by a wavelength filter 37 that transmits the fluorescent radiation and blocks the excitation radiation.

Figure 2:
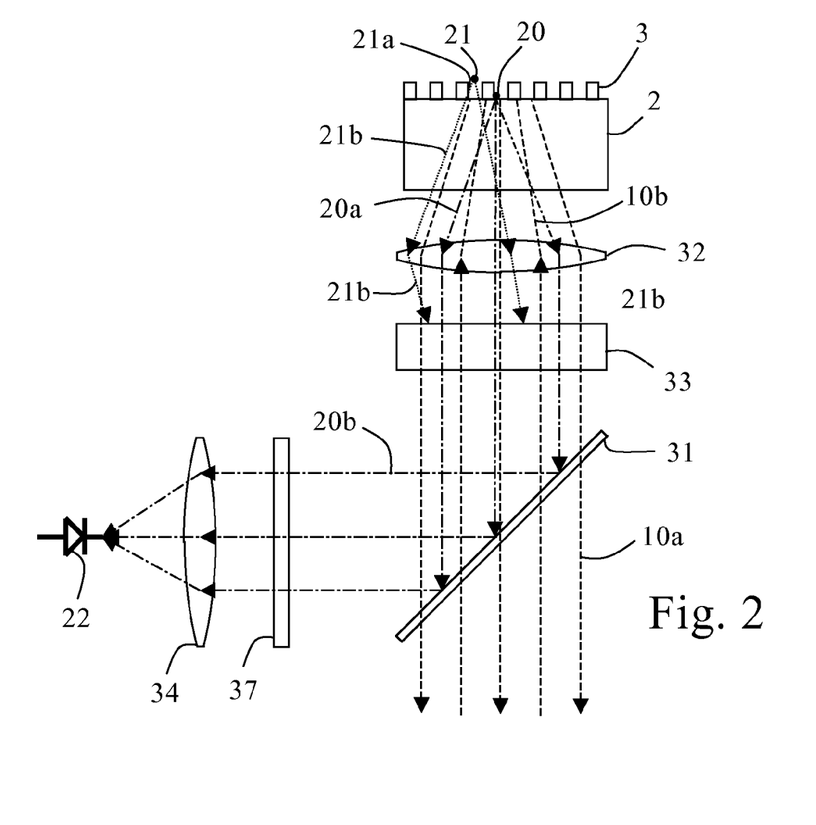
FIG. 2 is a schematic illustration of an embodiment of a biosensor.

FIG. 2 discloses an embodiment, comprising a substrate 2 of glass provided with a wiregrid 3 of a metal, such as aluminum, gold, silver, chromium, etc. The wiregrid comprises apertures in the form of slits having a first in-plane dimension (width) less than the diffraction limited width 270 nm, such as 70 nm. The slit has a second in-plane dimension (length), larger than the diffraction limited width, such as 1 mm. A target molecule having a fluorophore 20 is immobilized/binds at the substrate end of the aperture and another fluorophore 21 is present in a fluid 5 present at the analyte end of the aperture.

Excitation radiation, such as light having a wavelength in vacuum of about 700 nm, indicated by arrows 10b, is directed from a source towards a dichroic mirror 31. From the dichroic mirror 31, the excitation radiation passes said polarization filter 33 to a lens 32 for focusing the polarized excitation radiation 10b towards the biosensor surface.
The excitation radiation influences the fluorophores to emit radiation. Emitted radiation 20a from fluorophore 20 present at the substrate side of the aperture will pass through the lens 32 and through the polarizing filter 33, passing only R-polarized radiation 20b. The passed radiation 20b will be reflected by the dichroic mirror 31 towards lens 34 and a detector 22. The R-polarized excitation radiation 10b at the substrate side of the aperture forms an evanescent field inside the apertures having an exponential decay. The excitation radiation will be attenuated by said attenuation factor η and only a small fraction of the excitation radiation will reach the fluorophore 21 at the analyte side of the aperture. The fluorophore 21 will emit radiation 21a, which will pass the aperture and reach the lens 32 and the polarizing filter 33. The T-polarized component 21b of the radiation from fluorophore 21 will pass the apertures, but will be blocked by the polarizing filter 33. The R-polarized component of the radiation from fluorophore 21 will be attenuated when passing the aperture by said attenuation factor η and will pass through lens 32, polarizing filter 33 and be directed by the dichroic mirror 31 towards the lens 34 and the detector 22. Thus, the background radiation from fluorophore 21 will be attenuated by a factor η^2 compared to the situation without the polarizing filter 33.

The polarizing filter 33 can be aligned with the wiregrid at the setup of the biosensor, by measuring the level of the excitation radiation at the analyte side of the apertures. When the this-way measured excitation radiation level is at minimum, the polarizing filter 33 is aligned with the wiregrid, meaning that the polarizing filter passes only radiation having a polarization perpendicular to the wiregrid.

By rotating the polarizing filter, the background reduction can be made variable. This improves flexibility, since orientation of the external polarizing filter can be rotated, which allows not only to suppress the background but also to measure the background and to determine the polarization state of the bound fluorophores.

Figure 3:
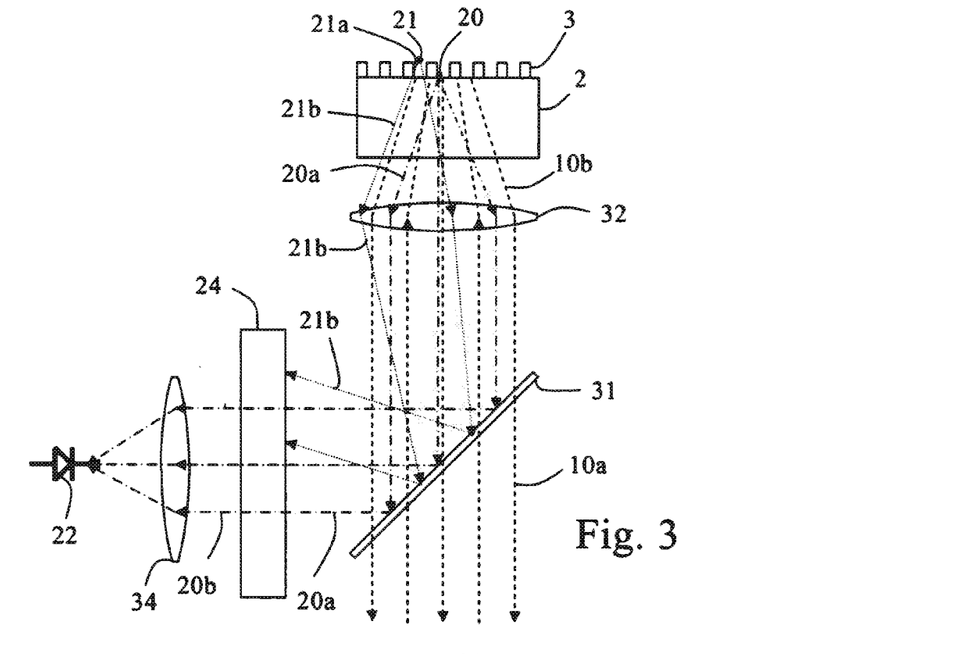
FIG. 3 is a schematic illustration of another embodiment of a bio sensor.

FIG. 3 discloses another embodiment, in which the polarizing filter 24 is only passed by the radiation emitted by the fluorophores. In this case, the polarizing filter 24 does not need to be transparent for the excitation radiation, which may be relevant for fluorophores with large Stokes shift, such as larger than 100 nm. The excitation radiation may have a circular polarization. Alternatively, the excitation may be linearly-polarized radiation, in which case the polarization should be aligned as indicated above.

Figure 4:
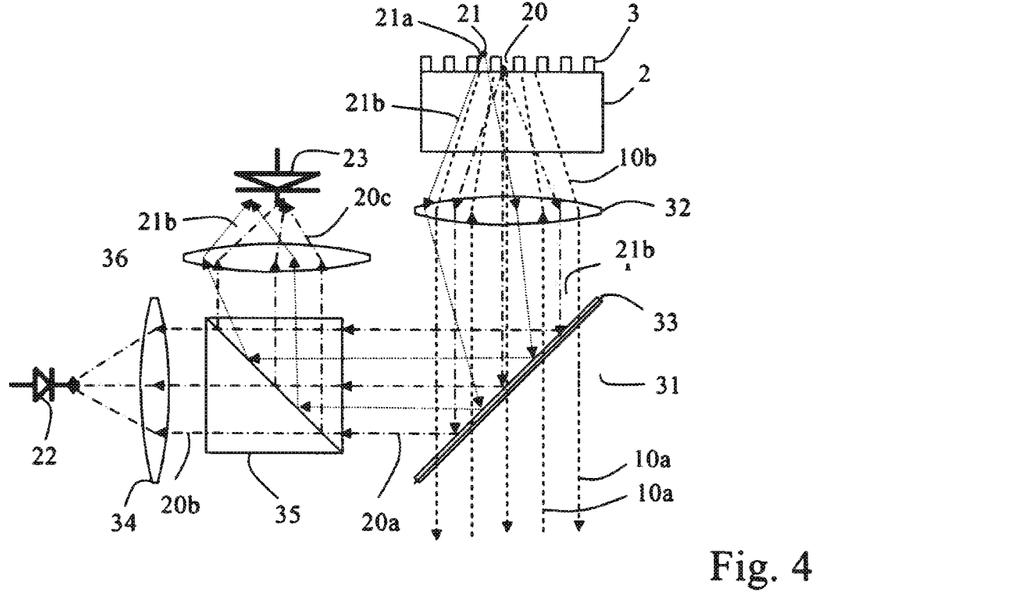
FIG. 4 is a schematic illustration of a further embodiment of a biosensor

FIG. 4 discloses a further embodiment, in which the polarizing filter 24 of the embodiment of FIG. 3 is replaced by a polarizing beam splitter 35. The polarizing beam splitter 35 passes R-polarized radiation 20b to lens 34 and detector 22, while the polarizing beam splitter 35 directs T-polarized radiation 20c and 21b to a second lens 36 and a second detector 23. Thus, the background signal can be estimated.

Figure 5:
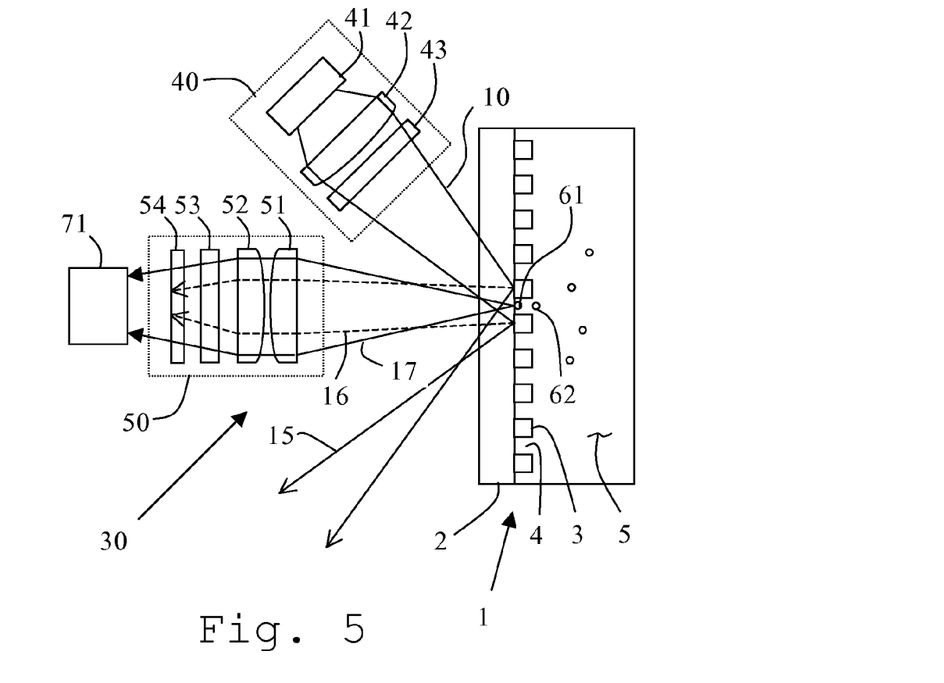
FIG. 5 is a schematic block diagram of a yet further embodiment of the invention.

FIG. 5 shows another embodiment of the biosensor 1, which is exposed to excitation radiation 10 from an external radiation source, comprising for example ultraviolet, visible or infrared light. The radiation source is included in a detection device 30, which is separate from the biosensor 1 defined above.

In the present embodiment, a non-polarized light source is used, such as one or several LED:s. Such a light source may emit larger power of excitation radiation and is much cheaper than a laser source.

The light source unit 40 comprises one or several LEDs 41 that emit radiation around a wavelength of 630 nm, a lens 42 and a pass filter 43 for passing excitation light and for removing light that overlaps the emission band of the fluorescent labels and the pass band of emission filter 54. Thus, the filter may have a pass-band which is typically 20 to 30 nm wide and transmits light 10 that overlaps the absorption or excitation band of the fluorescent labels. An example of a suitable pass-band wavelength range for these LEDs is 620 to 650 nm; a suitable pass filter is the 3RD Millenium 620-650 filter available from Omega Optical, Inc.

The light is directed towards the biosensor from the substrate side at an angle and the light is partially reflected by the wire grid, as shown by light beam 15. Thus, substantially no excitation light reaches a sensor 71. Only a small fraction of scattered excitation light is directed towards the sensor 71, as shown by broken lines 16.

An imaging block 50 is arranged at substantially right angle to the biosensor at the back side thereof. The imaging block 50 comprises a first lens 51 and a second lens 52 for directing emission radiation 17 towards a detector 71 via a polarizer 53 and one or several emission filters 54, which pass emission radiation 17 and block excitation radiation 16, if any. For fluorescent labels such as atto-680 dye or Fluor 633 dye, which have emission spectra with a spectral width of about 50 nm centred around wavelength of 700 nm and 650 nm, respectively, suitable transmission wavelengths for the emission filters 54 have a minimum transmission wavelength of 660 nm or larger, such as the 695AF55 Emitter XF3076 filter available from Omega Optical, Inc, which has a minimum transmission wavelength of 665 nm.

The detector 71 may be a camera comprising a CCD or a CMOS detector. Further alternatives appear below.

In case of non-polarized light, the excitation radiation can be decomposed into T- and R-polarized radiation. As a result, about half of the excitation radiation is substantially transmitted through the wire grid and the other half of the excitation radiation generates an evanescent field inside the aperture that decays exponentially and is essentially not transmitted. Only a small fraction of the R polarized radiation will pass through the aperture. Thus, the wire grid operates substantially as a polarization filter.

The ratio between the radiation passing the wire grid and the radiation impinging on the wire grid is called the extinction rate, and is typically about 0.001 for R polarized radiation for a typical wiregrid.

The radiation will excite the fluorescent labels to emit fluorescent radiation. For an ensemble of fluorophores, the labels may emit about 75% of the same polarization as the excitation radiation polarization.

The fluorescent labels 61 positioned in the aperture adjacent to the substrate end of the aperture is excited by excitation radiation having T and R polarization, wherein T normally is approximately equal to R for unpolarized excitation light. The total excitation radiation is T+E which results in a fluorescent emission from the labels. The emission will be in all directions and it is assumed that 50% will be directed towards the detector.

A fluorescent label 62 positioned outside the aperture adjacent to the front side or sample side of the biosensor will be excited by the T component of the excitation light which passes the wire grid almost unattenuated. In addition, the R component of the excitation light will be attenuated by the extinction factor n. Thus, the T component and the R component will result in emission radiation. This emission will be in all directions and it is assumed that 50% will reenter into the aperture towards the detector. However, the R component will be attenuated by the extinction factor n. Finally, the polarization filter will reduce the T component by a factor N. The ratio between the detected fluorescence that originate from labels 61 and 62 after the polarization filter is:

$$(N+1)/[(N*\tfrac{3}{4}+n*\tfrac{1}{4})+n*(n*\tfrac{3}{4}+N*\tfrac{1}{4})]$$

If it is assumed that N=n, than the ratio will be 1/n, which demonstrates that the first embodiment of the present invention results in a background suppression similar to the extinction ratio of a wire grid. If N<<n, the ratio will be about 4/n. A typical extinction ratio of a wiregrid is n=0.001.

The polarization filter 53 can have an extinction factor N of at least the same as said wiregrid extinction factor n, but may have a still smaller extinction factor of less than about 0.1*n. Such polarizing filters are commercially available, such as Glan-laser polarizers with a typical extinction factor of 10^−5.

The polarization filter 53 may be a wiregrid similar to the wiregrid 1, in which case the polarizing filter 53 has the same extinction factor n as the wiregrid.

Excitation radiation scattered from the substrate 2 and the wiregrid would also reach the detector as background radiation. Such excitation background radiation is reduced by emission filter 54, which attenuates light with a wavelength shorter than the emission wavelength, and thus essentially blocks the excitation light.

The embodiment according to FIG. 5 operates in reflection mode, in which the light source and the detector both are arranged at the back side of the biosensor and the fluid to be detected is on the opposite side of the wires on the substrate. The light is directed towards the substrate with an angle larger than the numerical aperture of the first lens 51 in order to be reflected in another direction than towards the detector.

Figure 6:
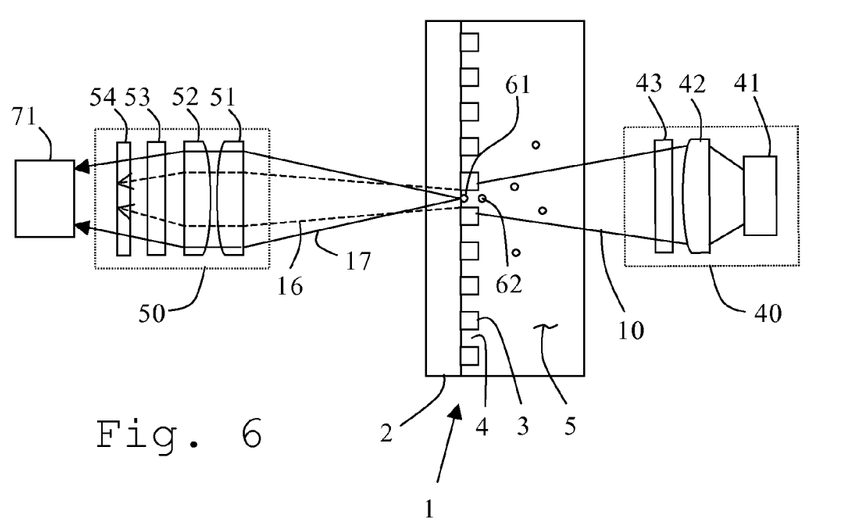
FIG. 6 is a schematic block diagram of a still further embodiment of the invention.

FIG. 6 discloses another embodiment, with a wire grid having apertures similar to the first embodiment, operating in transmission mode, in which the light source is arranged at the front side of the biosensor and the detector is arranged at the back side of the biosensor. The operation is similar to the embodiment according to FIG. 5.

Light emitted by the LED 41 is focused by a lens 42 and illuminates an aperture or a plurality of apertures of the grid after passing the pass filter 43. The excitation light having T polarization will pass the aperture essentially unattenuated, while the excitation light having R polarization will be substantially blocked.

The excitation light passing through the aperture will essentially be T polarized excitation light, which is substantially blocked by the polarization filter 53. Any T polarized excitation light still passing through the polarization filter 53, and attenuated by the extinction rate N, and any R polarized excitation light still passing the wiregrid, and attenuated by the extinction rate n, will be blocked by the pass filter 54, which may comprise several cascaded filter, before reaching the detector 71.

The fluorescent label 61 positioned at the substrate end of the aperture will be excited substantially only by the T component of the excitation light, which means that it will emit about half of the emission radiation of the first embodiment in FIG. 5.

The background label 62 positioned outside the aperture adjacent to the sample end of the aperture will emit emission radiation. The T component will pass and the R component will be reduced by the extinction factor n.

Thus the ratio between the emission of the substrate end label 61 and the sample end label 62 reaching the detector will be:

$$(N*\tfrac{3}{4}+\tfrac{1}{4}+n*\tfrac{3}{4}+N*n*\tfrac{1}{4})/(N+n)$$

If N=n, and n<<1 (typical value for n=0.001), the ration will be about 1/(8*n).

If n<<1, and N<<n (that is a polarizer 53 with an extinction ratio substantially smaller than the wire grid), the ratio will be about 1/(4*n).

Figure 7:
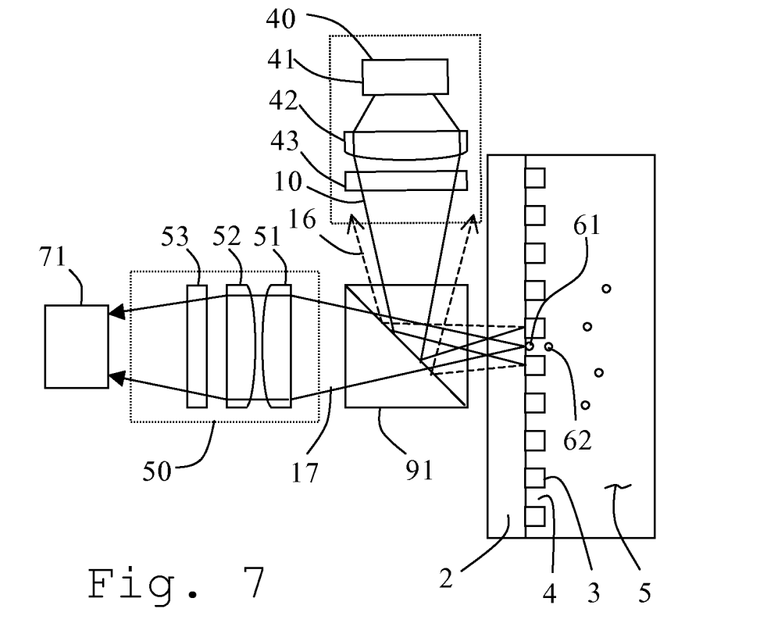
FIG. 7 is a schematic block diagram of a still yet further embodiment of the invention.

In another embodiment, the excitation radiation is directed towards the wiregrid essentially parallel to the substrate, as shown in FIG. 7. A dicroic mirror 91 is arranged in the light path of, for example, the LED light and redirect the light perpendicular towards the substrate. The dicroic mirror is designed to reflect the excitation light at wavelength 620 to 650 nm and pass emission light at wavelengths larger than 670 nm. Thus, the emission filter 54 may be dispenced with as indicated in FIG. 7, but the emission filter 54 may be included if the dicroic mirror still passes a small fraction of the excitation light.

The polarizing filter 53 can be aligned with the wiregrid at the setup of the biosensor, for example by illumination of the wiregrid from the sample-end (i.e. via the fluid on top) and minimizing the power on the detector 71. When the this-way measured power is at minimum, the polarizing filter 53 is aligned with the wiregrid, i.e. arranged perpendicular to the wiregrid, meaning that the polarizing filter passes only radiation having R polarization perpendicular to the plane of transmission of the wiregrid.

By rotating the polarizing filter, the background reduction can be made variable. This improves flexibility, since orientation of the external polarizing filter can be rotated, which allows not only to suppress the background but also to measure the background and to determine the polarization state of the bound fluorophores.

Figure 8:
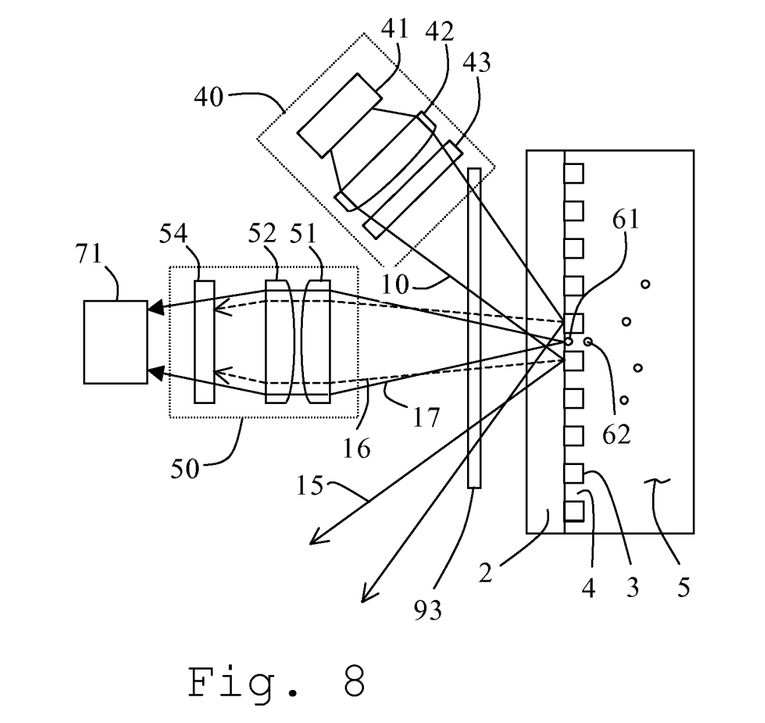
FIG. 8 is a schematic block diagram of a still another embodiment of the invention.

FIG. 8 discloses a further embodiment, in which the polarizing filter 93 is arranged in another position compared to the embodiment of FIG. 5, namely between the imaging block 50 and the substrate 2. In addition, the polarizing filter 93 is arranged between the light unit 40 and the substrate so that the light from the LED:s 41 passes the polarization filter 93 before reaching the substrate. Thus, the excitation light from the LED:s to the substrate and the emission light from the fluorescent labels passes through the same polarizing filter 93. The polarzising filter is arranged in such a position that the excitation light being non-polarized passes through the polarization filter 93, which passes R polarized radiation but attenuates T polarized radiation by a factor N, which may be $10^{-3}$ to $10^{-6}$. The fluorescent label 61 positioned at the substrate end of the aperture and the fluorescent label 62 positioned at the sample end of the aperture will emit emission radiation. When passing back through the aperture, the R component will be further attenuated by a factor n, and when passing through the polarization filter, the T component will be attenuated by a factor N. The ratio between the emission radiations from label 61 and label 62 after the polarization filter is:

$$(3/4+N*1/4)+(N*N*3/4+N*1/4)/(n*n*3/4+N*n*1/4)+(N*N*3/4+n*N*1/4)$$

If N=n, the ratio will be $3/(8*n*n)$
If N<<n, the ratio will be about $1/(n*n)$.

The polarization filter 93 is arranged with the polarization direction perpendicular to that of the wiregrid. If the polarization filter 93 is a wiregrid, the grid direction of the filter should be perpendicular to the grid direction of the wiregrid.

Figure 9:
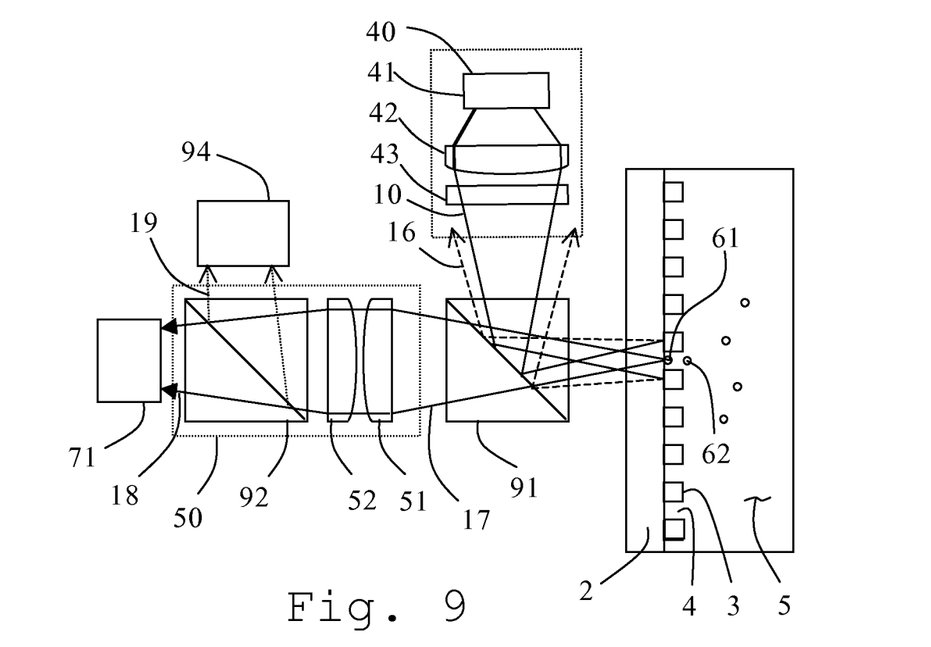
FIG. 9 is a schematic block diagram of a yet another embodiment of the invention.

As shown in FIG. 9, the polarization filter 53 of the embodiment of FIG. 7 can be replaced by a polarizing beam splitter 92. The polarizing beam splitter 92 passes R polarized radiation 18 to the detector 71, while the polarizing beam splitter 92 directs T-polarized radiation 19 on to a second detector 94. Thus, the background signal can be measured. The polarizing beam splitter 92 may replace the polarization filter 53 also in the embodiments according to FIGS. 1 and 2.

Figure 10:
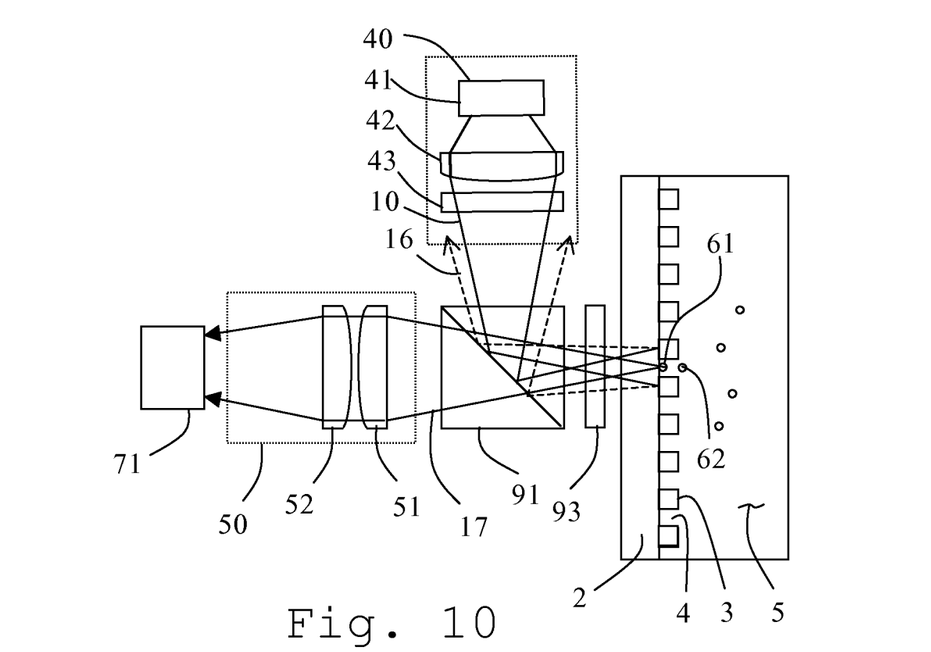
FIG. 10 is a schematic block diagram of a still yet another embodiment of the invention.

FIG. 10 shows a further embodiment, similar to FIG. 7 or FIG. 9, in which the polarization filter is arranged in the same position as in the embodiment of FIG. 8, i.e. close to the substrate. Thus, excitation light from the un-polarized light sourde 41 is directed towards the dicroic mirror 91 and reflected towards the substrate via the polarization filter 93, which substantially only passes R polarized radiation. The excitation radiation results in fluorescence emission radiation from the fluorophore label 61, which passes through the polarization filter 93, the dicroic mirror 91 to the detector 71, and from the fluorophore label 62, which passes through aperture, the polarization filter 93, the dicroic mirror 91 to the detector 71. The calculation of the ratio between the emission radiations from the fluorescent labels 61 and 62 is the same as for the embodiment of FIG. 8.

In the above-mentioned embodiments, a wiregrid biosensor of a simple and cheap construction can be used, which means that the wiregrid can be disposable.

The polarizing filter is arranged outside the biosensor and can be used several times. The polarizing filter is arranged without contact with the analyte to be examined. The polarizing filter is always arranged between the transparent substrate and the sensor. Thus, a more versatile polarizing filter can be used, resulting in a very large background radiation attenuation, without substantially increasing the total cost per analysis.

The different elements of the light source unit 40 and the imaging block 50 can be arranged in other orders than indicated above. Thus, the excitation radiation pass filter 43 can be arranged between the light source 41 and the lens 42. In the embodiment of FIG. 7, the dicroic mirror can be arranged to perform the operation of the pass filter 43, which becomes superfluous and can be dispenced with. In the imaging block 50, the elements order can be different. For example, the polarization filter may be arranged in any position between the substrate and the detector 71.

The embodiment according to FIG. 5 was used in a test environment having the following properties:

In order to demonstrate the background suppression, samples with a honeycomb pattern of labelled proteins have been fabricated by sputtering a chess board pattern of SiO2 spacer material on the wire grid, followed by immobilization of proteins labelled with Fluor 633 dye on the portions of the transparent substrate 2 that overlap with the apertures 4 and that are not covered by the spacer material. On top of the fabricated samples were attached 0.5 mm thick hybridization chambers filled with a very high concentration, such as 4.5 micro molar, of a dye solution, such as atto-680 dye, available from available from Atto-Tec GmbH. These samples were characterized in a set-up similar to the set-up of FIG. 1, using 4 red LEDs spectrally filtered to limit the excitation wavelengths between 620 to 650 nm. By rotating the transmission axis of the polarizer, it was possible to switch the detection volume from essentially evanescent or near field to essentially the complete hybridization chamber.

Figure 11:
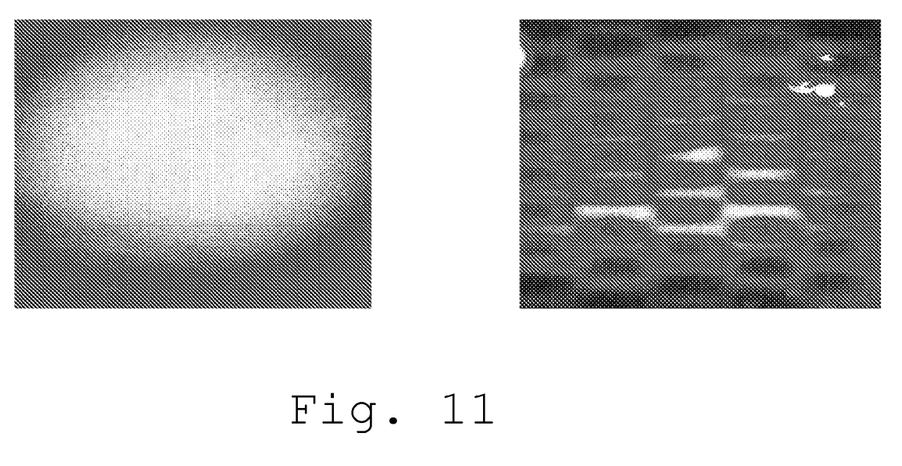
FIG. 11 includes two photographs showing a detector picture with a polarization filter arranged in parallel with and perpendicular, respectively, to a wiregrid that is covered with a pattern of labelled molecules.

FIG. 11 shows the measured fluorescence images: To the left, the measured fluorescence images for the polarizer being parallel to the transmission axis of the wiregrid and to the right for the polarizer to be orthogonal to the transmission axis of the wire grid. The detection volume was limited to essentially only the labelled proteins on the substrate-end of the aperture and a small evanescent volume of dye solution with a height of only 20-30 nm. Integration time for the left image is about a factor 500 smaller than for right image. From FIG. 11, it can be clearly seen that the background generated by the fluorescent fluid on top of the wire grid can efficiently be suppressed The fact that the integration time for the left image is about a factor 500 smaller, clearly demonstrates that it is possible to suppress background fluorescence that is substantially larger than the signal.

Moreover, in the embodiment according to FIG. 5, dark field illumination of the wire grid is used where the angle of incidence of the incident light is larger than the angle corresponding with the numerical aperture of the collection lens used for imaging on the detector. This way, the specularly reflected light is not imaged on the detector.

The present embodiments have one or several of the following advantages:

Critical alignment between polarization axis of excitation source and transmission axis of wire grid is no longer required. In previous embodiments, the polarization axis of source has to be aligned orthogonal to the transmission axis of the wire grid to generated a purely evanescent field in the space between the wires.

Lasers are typically more expensive than un-polarized sources. For applications such as fluorescence, the absorption band of the label molecules is quite wide and this allows the use of LEDs. LEDs are especially attractive because they offer similar power levels as lasers at a substantially lower cost. Furthermore it is anticipated that the optical powers of LED will substantially increase in the future.

Polarization purity of a typical laser is 100:1, while typical extinction of wire grids used in wire grid biosensor concept is better than 1000. This implies that each laser requires a dedicated polarizer with extinction equal to or better than the extinction of the wire grid.

Long coherence length of a laser implies speckle and this limits uniformity of illumination. In the present embodiments, there is used a light source having low coherence length, such as a bandwith larger than 1 nm (please review this portion).

The embodiments can be used in different applications, such as an optical biosensor for measurement with high surface specificity as required for measurement in high background environment, e.g. DNA-hybridization assay with high multi-plex number.

The embodiments can be used as a microscope, wherein the sensor 71 essentially is replaced by the eye of the user.

Although the present invention has been described above with reference to specific embodiment, it is not intended to be limited to the specific form set forth herein. Rather, the invention is limited only by the accompanying claims and, other embodiments than the specific above are equally possible within the scope of these appended claims.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A device for monitoring radiation emitted by luminophores present in an analyte fluid, comprising:
   a biosensor having at least one non-transparent material arranged on a first side of a substrate of a transparent material and forming at least one aperture for being filled with said analyte fluid, the aperture having a first in-plane dimension which is smaller than half an effective wavelength of radiation in the biosensor and a second in-plane dimension which is larger than half an effective wavelength of radiation of the biosensor, and wherein the aperture provides a plane of transmission;
   an excitation source for exciting luminophores present in the analyte fluid of said biosensor, wherein the excitation source is disposed at a second side of the substrate opposite the first side so as to provide excitation radiation to the luminophores from the second side of the substrate;
   a detector for detecting radiation emitted by the luminophores upon excitation; and
   a polarizing filter arranged in between the biosensor and the detector, wherein the polarizing filter is arranged for substantially attenuating radiation with an electric field parallel to the plane of transmission of the aperture from reaching the detector and for substantially passing radiation with an electric field orthogonal to the plane of transmission of the aperture, wherein said excitation source is a light source emitting polarized light having an elliptical polarization.

2. The device according to claim 1, wherein said detector is arranged at the second side of the substrate.

3. The device according to claim 1, wherein said polarizing filter is rotatable.

4. The device according to claim 1, wherein said light source comprises a band pass filter for passing radiation having a wavelength pass band corresponding to an absorption wavelength band for excitation of said luminophores, and for blocking radiation having a wavelength corresponding to an emission wavelength of said luminophores.

5. The device according to claim 4, wherein a wavelength pass filter is arranged before the detector for passing radiation having a wavelength corresponding to an emission wavelength of said luminophores and blocking radiation passed by said band pass filter.

6. The device according to claim 1, wherein radiation from said light source is arranged to pass said polarizing filter before illuminating the biosensor.

7. The device according to claim 1, wherein said light source emits light having a bandwidth larger than about 1 nm.

8. The device according to claim 1, wherein the analyte fluid comprises a target molecule and a luminophore in a medium which is disposed in said aperture.

9. The device according to claim 8, wherein a capture molecule is arranged in the aperture at an end of the aperture adjacent the substrate, said capture molecule being configured to form an aggregate with said target molecule and luminophore.

10. The device of claim 1, wherein said polarizing filter comprises a dichroic mirror arranged to direct said excitation radiation towards the biosensor and to pass emission radiation to the detector.

11. A device for monitoring radiation emitted by luminophores present in an analyte fluid, comprising:
    a biosensor having at least one non-transparent material arranged on a first side of a substrate of a transparent material and forming at least one aperture for being filled with said analyte fluid, the aperture having a first in-plane dimension which is smaller than half an effective wavelength of radiation in the biosensor and a second in-plane dimension which is larger than half an effective wavelength of radiation of the biosensor, and wherein the aperture provides a plane of transmission;
    an excitation source for exciting luminophores present in the analyte fluid of said biosensor, wherein the excitation source is disposed at a second side of the substrate opposite the first side so as to provide excitation radiation to the luminophores from the second side of the substrate;
    a first detector for detecting radiation emitted by the luminophores upon excitation; and
    a polarizing filter arranged in between the biosensor and the first detector, wherein the polarizing filter is arranged for substantially attenuating radiation with an electric field parallel to the plane of transmission of the aperture from reaching the detector and for substantially passing radiation with an electric field orthogonal to the plane of transmission of the aperture, further comprising a second detector, wherein the polarizing filter comprises a polarizing beam splitter passing radiation having a polarization plane orthogonal with the transmission plane of the aperture towards the first detector, and directing radiation having a polarization parallel to the transmission plane of the aperture towards the second detector such that the second detector provides an output signal indicating a background radiation signal level.

12. A device for monitoring radiation emitted by luminophores present in an analyte fluid, comprising:
    a biosensor having at least one non-transparent material arranged on a first side of a substrate of a transparent material and forming at least one aperture for being filled with said analyte fluid, the aperture having a first in-plane dimension which is smaller than half an effective wavelength of radiation in the biosensor and a second in-plane dimension which is larger than half an effective wavelength of radiation of the biosensor, and wherein the aperture provides a plane of transmission;
    an excitation source for exciting luminophores present in the analyte fluid of said biosensor, wherein the excitation source is disposed at a second side of the substrate opposite the first side so as to provide excitation radiation to the luminophores from the second side of the substrate;
    a detector for detecting radiation emitted by the luminophores upon excitation; and
    a polarizing filter arranged in between the biosensor and the detector, wherein the polarizing filter is arranged for substantially attenuating radiation with an electric field parallel to the plane of transmission of the aperture from reaching the detector and for substantially passing radiation with an electric field orthogonal to the plane of transmission of the aperture, wherein the excitation light source emits circularly polarized light.

13. The device of claim 12, wherein said detector is arranged at the second side of the substrate.

14. The device of claim 12, wherein the analyte fluid comprises a target molecule and a luminophore in a medium which is disposed in said aperture.

15. The device of claim 12, wherein said polarizing filter comprises a dichroic mirror arranged to direct said excitation radiation towards the biosensor and to pass emission radiation to the detector.

16. The device of claim 12, wherein said light source comprises a band pass filter for passing radiation having a wavelength pass band corresponding to an absorption wavelength band for excitation of said luminophores, and for blocking radiation having a wavelength corresponding to an emission wavelength of said luminophores.

17. A device for monitoring radiation emitted by luminophores present in an analyte fluid, comprising:
   an excitation source configured to provide excitation radiation for exciting the luminophores present in the analyte fluid;
   a biosensor having a metal wire grid arranged on a first side of a substrate of a transparent material, wherein the metal wire grid forms at least one aperture for being filled with the analyte fluid, wherein the aperture has a first in-plane dimension which is smaller than half an effective wavelength of the excitation radiation and a second in-plane dimension which is larger than half an effective wavelength of the excitation radiation, and wherein the aperture provides a plane of transmission for the excitation radiation;
   a capture molecule arranged in the aperture at an end of the aperture adjacent the substrate, the capture molecule being configured to form an aggregate with a target molecule and a luminophore in the analyte fluid;
   a first detector for detecting radiation emitted by the luminophores upon excitation, the first detector being disposed at a second side of the substrate opposite the first side;
   a polarizing filter arranged in between the biosensor and the first detector, wherein the polarizing filter is arranged for substantially attenuating radiation with an electric field parallel to the plane of transmission of the aperture from reaching the detector and for substantially passing radiation with an electric field orthogonal to the plane of transmission of the aperture; and
   a second detector, wherein the polarizing filter comprises a polarizing beam splitter passing radiation having a polarization plane orthogonal with the transmission plane of the aperture towards said first detector and directing radiation having a polarization parallel to the transmission plane of the aperture towards the second detector such that the second detector provides an output signal indicating a background radiation signal level.

18. The device of claim 17, wherein the excitation source is disposed at the second side of the substrate so as to provide excitation radiation to the luminophores from the second side of the substrate.

19. The device of claim 17, wherein the excitation source is disposed at the first side of the substrate so as to provide excitation radiation to the luminophores from the first side of the substrate.

20. The device of claim 17, wherein the polarizing filter is disposed in an optical path between the excitation source and the biosensor, such that the excitation radiation passes through a same physical structure of the polarizing filter when travelling from the excitation source to the biosensor as the radiation emitted by the luminophores does when travelling from the luminophores to the first detector.

* * * * *